United States Patent
Laute et al.

(10) Patent No.: US 12,159,710 B2
(45) Date of Patent: Dec. 3, 2024

(54) APPARATUS FOR IMPLEMENTING A CLINICAL PROTOCOL

(71) Applicant: KONINKLIJKE PHILIPS N.V., Eindhoven (NL)

(72) Inventors: Niels Laute, Venlo (NL); Elise Claude Valentine Talgorn, Eindhoven (NL); Rik August Runge, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 243 days.

(21) Appl. No.: 17/794,742

(22) PCT Filed: Jan. 21, 2021

(86) PCT No.: PCT/EP2021/051320
§ 371 (c)(1),
(2) Date: Jul. 22, 2022

(87) PCT Pub. No.: WO2021/148527
PCT Pub. Date: Jul. 29, 2021

(65) Prior Publication Data
US 2023/0110532 A1    Apr. 13, 2023

(30) Foreign Application Priority Data
Jan. 22, 2020 (EP) .................................... 20153060

(51) Int. Cl.
*G16H 40/63* (2018.01)
*G16H 40/40* (2018.01)
(52) U.S. Cl.
CPC ............. *G16H 40/63* (2018.01); *G16H 40/40* (2018.01)

(58) Field of Classification Search
CPC ............................. G16H 40/63; G16H 40/40
USPC .......................................................... 705/2–3
See application file for complete search history.

(56) References Cited

U.S. PATENT DOCUMENTS

| | | | |
|---|---|---|---|
| 9,652,128 B2 * | 5/2017 | Shin | G06T 7/73 |
| 9,672,648 B2 * | 6/2017 | Park | G06F 11/328 |
| 11,007,020 B2 * | 5/2021 | Ziraknejad | G06F 3/011 |

(Continued)

FOREIGN PATENT DOCUMENTS

WO    WO-2018148845 A1 *    8/2018    ............. A61B 34/25

OTHER PUBLICATIONS

International Search Report and Written Opinion for PCT/EP2021/051320, Mailing date: Apr. 26, 2021, 10 pages.

*Primary Examiner* — Michael Tomaszewski

(57) ABSTRACT

There is provided an apparatus (100) for implementing a clinical protocol. The apparatus (100) comprises one or more processors (102) configured to detect that a clinical protocol is to be implemented and identify which of a plurality of devices are required to implement the clinical protocol and one or more actions to perform in connection with the identified ones of the devices to implement the clinical protocol. The one or more processors (102) are configured to control a user interface (104) to output one or more notifications on the manner in which a user is to interact with one or more of the identified ones of the devices and/or control one or more of the identified ones of the devices to cause the one or more identified actions to be performed in connection with the identified ones of the devices to implement the clinical protocol.

14 Claims, 3 Drawing Sheets

(56) References Cited

U.S. PATENT DOCUMENTS

| | | | | |
|---|---|---|---|---|
| 2007/0001839 A1* | 1/2007 | Cambre | ................ | G06Q 10/08 |
| | | | | 340/539.12 |
| 2008/0077444 A1* | 3/2008 | MacLeod | ............... | G16H 40/20 |
| | | | | 604/189 |
| 2013/0066647 A1* | 3/2013 | Andrie | ................... | G16H 20/40 |
| | | | | 705/2 |
| 2014/0223349 A1* | 8/2014 | Shin | ........................ | G06T 7/73 |
| | | | | 715/771 |
| 2014/0236608 A1* | 8/2014 | Miklautsch | .......... | G06Q 10/087 |
| | | | | 705/2 |
| 2015/0109334 A1* | 4/2015 | Park | ........................ | G06T 11/60 |
| | | | | 345/633 |
| 2015/0370997 A1* | 12/2015 | Krongrad | ............ | G06Q 30/0629 |
| | | | | 705/2 |
| 2017/0243157 A1* | 8/2017 | Piron | ...................... | G16H 40/20 |
| 2018/0024362 A1* | 1/2018 | Williamson | .......... | G06T 19/006 |
| | | | | 345/428 |
| 2018/0289434 A1* | 10/2018 | Palo | ........................ | G16H 10/60 |
| 2019/0183591 A1* | 6/2019 | Johnson | ................. | B25J 9/1666 |
| 2022/0223260 A1* | 7/2022 | Masson | ............ | G06Q 10/06375 |

\* cited by examiner

APPARATUS FOR IMPLEMENTING A CLINICAL PROTOCOL

This application is the U.S. National Phase application under 35 U.S.C. § 371 of International Application No. PCT/EP2021/051320, filed on Jan. 21, 2021, which claims the benefit of European Application 20153060.7, filed Jan. 22, 2020. These applications are hereby incorporated by reference herein.

FIELD OF THE INVENTION

The disclosure relates to an apparatus and a computer-implemented method for implementing a clinical protocol.

BACKGROUND OF THE INVENTION

In hospitals, and intensive care units (ICUs) in particular, clinical staff need to interact with many different devices. Often, each device serves an individual purpose, while also being used together with one or more other devices for certain procedures. Next to this, the average lifespan of medical devices can be 10 to 20 years and updating the interface of these devices can be difficult since it often requires Food and Drug Administration (FDA) approval and additional training for the users of the devices, e.g. medical personnel (such as nurses, doctors, etc.). As a result, there are many situations that exist where users need to interact with multiple devices at the same time, which may come from different vendors and can be introduced at different times.

This means that the interaction paradigm is different for each device. Also, the look and/or feel of the interface of each device can be completely different. This makes it difficult for users to effectively and efficiently interact with multiple devices to perform a clinical protocol, especially when the devices are used simultaneously, which can occur often when a certain task needs to be fulfilled (e.g. using various medical devices). It can be particularly troublesome for less experienced users that are unfamiliar with the devices and extensive training is required, which is time consuming and expensive. In addition, for vendors of medical equipment, this can also be troublesome since modernizing and maintaining a consistent user experience (UX) over time is challenging. This is especially the case for hardware modifications but, even in the case of software, re-skinning the user interface (e.g. in terms of the look and feel) requires additional FDA approval.

WO 2018/148845 discloses a system in which a graphical user interface (GUI) is overlaid on a medical image display, where the display itself is medical equipment that is controlled by the system. The GUI overlay corresponds to an image and this image is overlaid on the same display on which medical images are displayed. A practitioner can look down at a projected three-dimensional control menu for interactions or use the GUI overlay corresponding to the image on the medical image display to do the same. However, this system still suffers from the above-described issues as it may still be necessary for the practitioner to interact with multiple devices to perform a clinical protocol and each of these devices will have different interactions for controlling them. This can be confusing for the practitioner, especially when the practitioner is required to interact with multiple devices simultaneously to perform a clinical protocol.

SUMMARY OF THE INVENTION

As noted above, the limitations with existing techniques is that it is difficult for users to effectively and efficiently interact with multiple different devices, especially when the devices are used simultaneously, to perform a clinical protocol. It would therefore be valuable to have an improvement aimed at addressing these limitations.

Therefore, according to a first aspect, there is provided an apparatus for implementing a clinical protocol. The apparatus comprises one or more processors. The one or more processors are configured to detect that a clinical protocol is to be implemented and identify which of a plurality of devices are required to implement the clinical protocol and one or more actions to perform in connection with the identified ones of the plurality of devices to implement the clinical protocol. The one or more processors are configured to control a user interface to output one or more notifications on the manner in which a user is to interact with one or more of the identified ones of the plurality of devices and/or control one or more of the identified ones of the plurality of devices to cause the one or more identified actions to be performed in connection with the identified ones of the plurality of devices to implement the clinical protocol.

In some embodiments, the user interface may be separate to the plurality of devices.

In some embodiments, the one or more processors may be configured to identify which of a plurality of devices are required to implement the clinical protocol by being configured to compare the clinical protocol to a plurality of clinical protocols stored in one or more memories with an indication of at least one device that is required to implement the clinical protocol and one or more actions that the at least one device is required to perform to implement the clinical protocol.

In some embodiments, the one or more processors may be configured to control the user interface to output the one or more notifications in an order that is defined by the clinical protocol and/or control one or more of the identified ones of the plurality of devices in an order that is defined by the clinical protocol.

In some embodiments, the one or more processors may be configured to control the user interface to output the one or more notifications in a plurality of different steps and/or control one or more of the identified ones of the plurality of devices in a plurality of different steps.

In some embodiments, the one or more processors may be configured to check at least one memory that is configured to store an indication of which of a plurality of devices is available to identify which of the identified ones of the plurality of devices are available and, only for the identified ones of the plurality of devices that are available, control the user interface to output the one or more notifications and/or control one or more of the identified ones of the plurality of devices.

In some embodiments, the one or more processors may be configured to control the user interface to output the one or more notifications next to the identified ones of the plurality of devices with which the user is to interact. In some embodiments, the user interface may comprise a virtual user interface and the one or more processors may be configured to render the virtual user interface over at least part of a user interface of one or more of the plurality of devices.

In some embodiments, the one or more processors may be configured to control one or more of the identified ones of the plurality of devices by being configured to transmit a signal to one or more of the identified ones of the plurality of devices to trigger the one or more of the identified ones of the plurality of devices to perform one or more of the identified actions. In some embodiments, the signal may comprise an application programming interface or a technical protocol for use by the one or more of the identified ones of the plurality of devices in performing the one or more of the identified actions.

In some embodiments, the one or more processors may be configured to acquire, from at least one sensor, a signal indicative of one or more actions of the user and control the user interface to render guidance based on the one or more actions of the user to guide the user in their interaction with one or more of the identified ones of the plurality of devices.

In some embodiments, the one or more actions to perform in connection with the identified ones of the plurality of devices to implement the clinical protocol may comprise one or more actions that the identified ones of the plurality of devices are required to perform to implement the clinical protocol and/or one or more actions that the user is required to perform in connection with the identified ones of the plurality of devices to implement the clinical protocol.

In some embodiments, the one or more processors may be configured to control the user interface to render a request as to whether the clinical protocol is to be implemented.

According to a second aspect, there is provided a method for implementing a clinical protocol. The method comprises detecting that a clinical protocol is to be implemented and identifying which of a plurality of devices are required to implement the clinical protocol and one or more actions to perform in connection with the identified ones of the plurality of devices to implement the clinical protocol. The method comprises controlling a user interface to output one or more notifications on the manner in which a user is to interact with one or more of the identified ones of the plurality of devices and/or control one or more of the identified ones of the plurality of devices to cause the one or more identified actions to be performed in connection with the identified ones of the plurality of devices to implement the clinical protocol.

According to a third aspect, there is provided a computer program product comprising a computer readable medium. The computer readable medium has computer readable code embodied therein. The computer readable code is configured such that, on execution by a suitable computer or processor, the computer or processor is caused to perform the method described earlier.

According to the aspects and embodiments described above, the limitations of existing techniques are addressed. In particular, the above-described aspects and embodiments provide an improved user experience by enabling a user to effectively and efficiently interact with multiple different devices, even when the devices are used simultaneously. This is made possible without the need to change any of the devices for consistency with others, which avoids the risk of destabilizing (e.g. the independent function of) devices since the devices can be left untouched without any changes or updates. Also, additional formal processes, such as FDA approval, can be avoided. The above-described aspects and embodiments allow a user to control multiple different devices with a single user interface, thereby reducing the complexity of operating the devices. The user can be guided (e.g. on a step-by-step basis) across different actions and devices with a single interface. The user is thus provided with simplified controls that are only relevant for a certain action, without changing the actual device and at the same time reducing menu or screen structures that are not necessary for the clinical protocol to be implemented. Moreover, as the user is provided with instructions on how to interact with one or more relevant devices and/or one or more relevant devices are controlled in the required way, even a less experienced or an untrained user can implement a clinical protocol easily and quickly. There is thus provided an improved technique for implementing a clinical protocol.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, there is provided herein an improved technique for implementing a clinical protocol.

Figure 1:
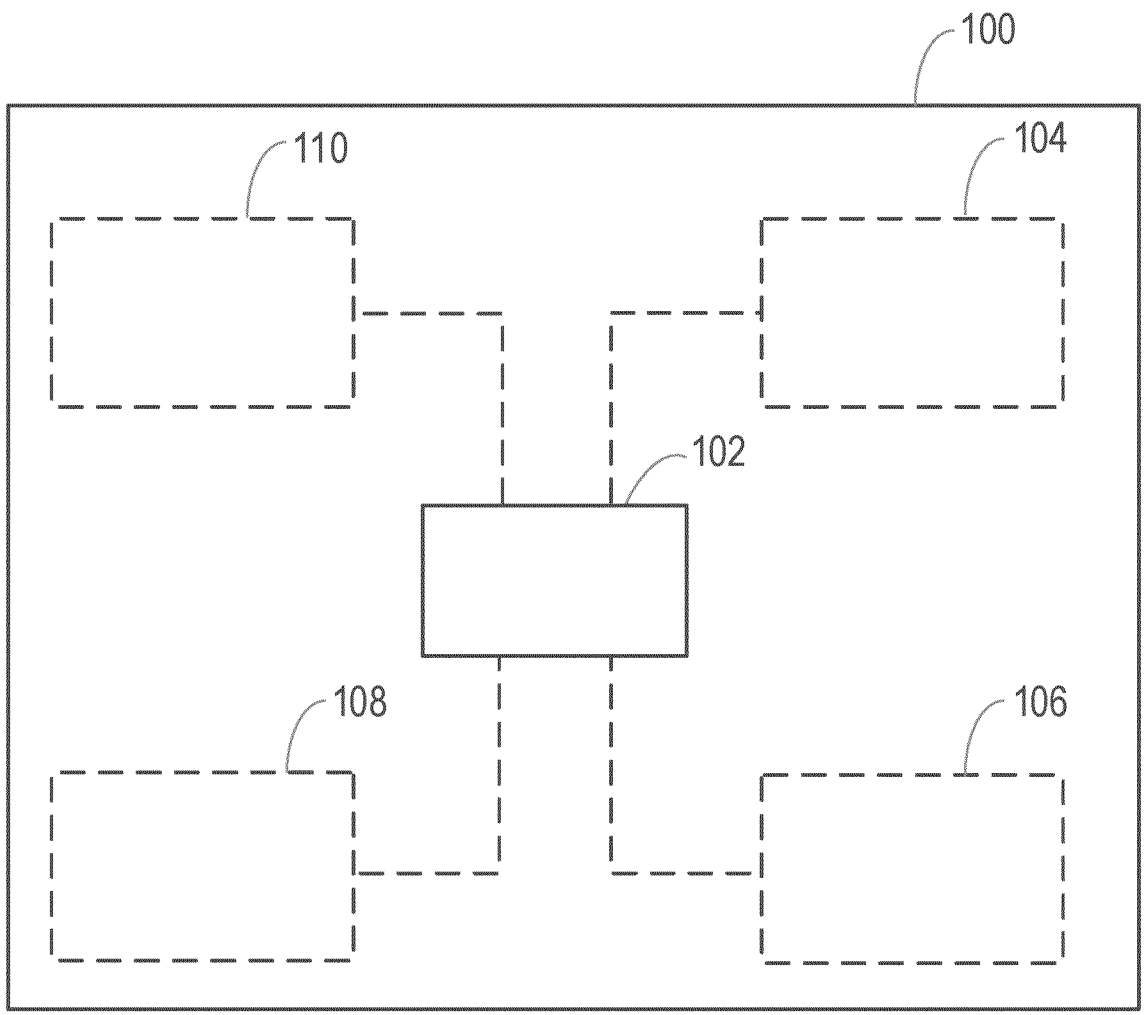
FIG. 1 is an illustration of an apparatus according to an embodiment.

FIG. 1 illustrates an apparatus 100 for implementing a clinical protocol according to an embodiment. As illustrated in FIG. 1, the apparatus 100 comprises one or more processors 102. The one or more processors 102 can be implemented in numerous ways, with software and/or hardware, to perform the various functions described herein.

In particular implementations, the one or more processors 102 can comprise a plurality of software and/or hardware modules, each configured to perform, or that are for performing, individual or multiple steps of the method described herein. The one or more processors 102 may comprise, for example, one or more microprocessors, one or more multi-core processors and/or one or more digital signal processors (DSPs), one or more processing units, and/or one or more controllers (e.g. one or more microcontrollers) that may be configured or programmed (e.g. using software or computer program code) to perform the various functions described herein. The one or more processors 102 may be implemented as a combination of dedicated hardware (e.g. amplifiers, pre-amplifiers, analog-to-digital convertors (ADCs) and/or digital-to-analog convertors (DACs)) to perform some functions and one or more processors (e.g. one or more programmed microprocessors, DSPs and associated circuitry) to perform other functions.

Briefly, the one or more processors 102 of the apparatus 100 are configured to, detect that a clinical protocol is to be implemented. The one or more processors 102 of the apparatus 100 are also configured to identify which of a plurality of devices (e.g. medical devices) are required to implement the clinical protocol and one or more actions to perform in connection with the identified ones of the plurality of devices to implement the clinical protocol. The one or more processors 102 of the apparatus 100 are further configured to control a user interface 104 to output one or more notifications on the manner in which a user is to interact with one or more of the identified ones of the plurality of devices and/or control one or more of the identified ones of the plurality of devices to cause the one or more identified actions to be performed in connection with the identified ones of the plurality of devices to implement the clinical protocol.

Herein, a clinical protocol can be any protocol (e.g. procedure) relating to the observation and/or treatment of a subject (e.g. patient). Herein, the user can be any user of the plurality of devices. For example, the user may be a medical professional (such as a doctor, a nurse, or any other medical professional), a carer, the subject, or any other user.

As illustrated in FIG. 1, in some embodiments, the apparatus 100 may comprise at least one user interface 104. Alternatively or in addition, in some embodiments, at least one user interface 104 may be external to (e.g. separate to or remote from) the apparatus 100. The one or more processors 102 of the apparatus 100 may be configured to communicate with and/or connect to at least one user interface 104. The one or more processors 102 of the apparatus 100 are configured to control at least one user interface 104 to operate in the manner described herein. In particular, the one or more processors 102 of the apparatus 100 are configured to control at least one user interface 104 to output the one or more notifications on the manner in which a user is to interact with one or more of the identified ones of the plurality of devices.

A user interface 104 can be configured to render (or output, display, or provide) information required by or resulting from the method described herein. For example, in some embodiments, at least one user interface 104 may be configured to render (or output, display, or provide), an indication of the detected clinical protocol is to be implemented, an indication of the identified ones of the plurality of devices, an indication of the one or more identified actions, the one or more notifications on the manner in which a user is to interact with one or more of the identified ones of the plurality of devices, and/or any other information, or any combination of information, required by or resulting from the method described herein. Alternatively or in addition, at least one user interface 104 can be configured to receive a user input. For example, at least one user interface 104 may allow the user to manually enter information or instructions, interact with and/or control the apparatus 100. Thus, at least one user interface 104 may be any one or more user interfaces that enable the rendering (or outputting, displaying, or providing) of information and/or enables the user to provide a user input.

For example, at least one user interface 104 may comprise one or more switches, one or more buttons, a keypad, a keyboard, a mouse, a graphical user interface (GUI) such as a display or screen (e.g. a touch screen, such as on a smart device), an application (e.g. on a smart device), or any other visual component, one or more speakers, one or more microphones or any other audio component, one or more lights (e.g. one or more light emitting diodes, LEDs), a component for providing tactile or haptic feedback (e.g. a vibration function, or any other tactile feedback component), an augmented reality device (e.g. augmented reality glasses configured to be worn by the user, or any other augmented reality device), a smart device (e.g. a smart mirror, a tablet, a smart phone, a smart watch, or any other smart device), or any other user interface, or combination of user interfaces. In some embodiments, one or more user interfaces that are controlled to render information may be the same as one or more user interfaces that enable the user to provide a user input.

As illustrated in FIG. 1, in some embodiments, the apparatus 100 may comprise at least one memory 106. Alternatively or in addition, in some embodiments, at least one memory 106 may be external to (e.g. separate to or remote from) the apparatus 100. For example, another apparatus may comprise at least one memory 106 according to some embodiments. In some embodiments, a hospital database may comprise at least one memory 106, at least one memory 106 may be a cloud computing resource, or similar. The one or more processors 102 of the apparatus 100 may be configured to communicate with and/or connect to at least one memory 106. The at least one memory 106 may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). In some embodiments, at least one memory 106 can be configured to store program code that can be executed by the one or more processors 102 of the apparatus 100 to cause the apparatus 100 to operate in the manner described herein.

Alternatively or in addition, at least one memory 106 can be configured to store information required by or resulting from the method described herein. For example, at least one memory 106 may be configured to store an indication of the detected clinical protocol is to be implemented, an indication of the identified ones of the plurality of devices, an indication of the one or more identified actions, the one or more notifications on the manner in which a user is to interact with one or more of the identified ones of the plurality of devices, and/or any other information, or any combination of information, required by or resulting from the method described herein. The one or more processors 102 of the apparatus 100 can be configured to control at least one memory 106 to store information required by or resulting from the method described herein.

As illustrated in FIG. 1, in some embodiments, the apparatus 100 may comprise at least one sensor 108. Alternatively or in addition, in some embodiments, at least one sensor 108 may be external to (e.g. separate to or remote from) the apparatus 100. For example, another apparatus may comprise at least one sensor 108 according to some embodiments. The at least one sensor 108 can, for example, be configured to acquire a signal indicative of one or more actions of the user. The at least one sensor 108 can be any one or more sensors capable of acquiring such a signal. For example, the at least one sensor 108 may comprise at least one motion sensor (e.g. a camera) configured to acquire a motion signal indicative of one or more actions of the user, or any other sensor, or any combination of sensors suitable for acquiring the signal indicative of one or more actions of the user. Although an example has been provided for the at least one sensor 108, a person skilled in the art will be aware of a variety of different sensors and combinations of sensors that may be suitable for acquiring the signal indicative of one or more actions of the user.

As illustrated in FIG. 1, in some embodiments, the apparatus 100 may comprise at least one communications interface (or communications circuitry) 110. Alternatively or in addition, in some embodiments, at least one communications interface 110 may be external to (e.g. separate to or remote from) the apparatus 100. A communications interface 110 can be for enabling the apparatus 100, or components of the apparatus 100 (e.g. the one or more processors 102, one or more user interfaces 104, one or more memories 106, and/or any other components of the apparatus 100), to communicate with and/or connect to each other and/or one or more other components. For example, one or more communications interfaces 110 can be for enabling the one or more processors 102 of the apparatus 100 to communicate with and/or connect to one or more user interfaces 104, one or more memories 106 and/or any other components of the apparatus 100.

A communications interface 110 may enable the apparatus 100, or components of the apparatus 100, to communicate and/or connect in any suitable way. For example, one or more communications interfaces 110 may enable the apparatus 100, or components of the apparatus 100, to communicate and/or connect wirelessly, via a wired connection, or via any other communication (or data transfer) mechanism. In some wireless embodiments, for example, one or more communications interfaces 110 may enable the apparatus 100, or components of the apparatus 100, to use radio frequency (RF), Bluetooth, or any other wireless communication technology to communicate and/or connect.

Figure 2:
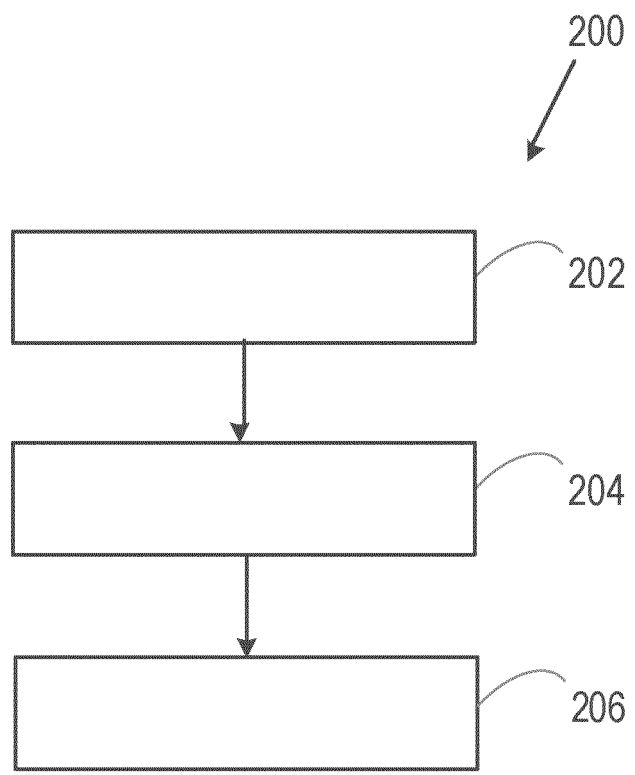
FIG. 2 is a flow chart illustrating a method according to an embodiment.

FIG. 2 illustrates a method 200 for implementing a clinical protocol according to an embodiment. More specifically, FIG. 2 illustrates a method 200 of operating the apparatus 100 described earlier with reference to FIG. 1 for implementing a clinical protocol. The method 200 illustrated in FIG. 2 is a computer-implemented method. As described earlier, the apparatus 100 comprises one or more processors 102. The method 200 illustrated in FIG. 2 can generally be performed by or under the control of the one or more processors 102 of the apparatus 100. The method can be at least partially automated. That is, at least part of or all of the method can be performed automatically.

With reference to FIG. 2, at block 202, it is detected that a clinical protocol is to be implemented. More specifically, the one or more processors 102 of the apparatus 100 detect that a clinical protocol is to be implemented. For example, in some embodiments, the one or more processors 102 of the apparatus 100 may be configured to acquire, from at least one sensor 108, a signal indicative of one or more actions of the user and detect that a clinical protocol is to be implemented based on the one or more actions of the user. As mentioned earlier, the apparatus 100 may comprise at least one sensor 108 and/or the at least one sensor 108 may be external to (e.g. separate to or remote from) the apparatus 100. In some embodiments, the one or more actions of the user may comprise one or more gestures of the user that indicate that the clinical protocol is to be implemented. The one or more processors 102 may be configured (e.g. pre-programmed) to recognize the one or more gestures in order to detect that a clinical protocol is to be implemented. Alternatively or in addition, in some embodiments, the one or more processors 102 of the apparatus 100 may be configured to detect that a clinical protocol is to be implemented upon expiry of a predetermined time period and/or upon detection of a predefined event.

In some embodiments, the one or more processors 102 of the apparatus 100 may be configured to control the user interface 104 to render a request as to whether the clinical protocol is to be implemented. For example, in some embodiments, the one or more processors 102 of the apparatus 100 may be configured to control the user interface 104 to render the request as to whether the clinical protocol is to be implemented in response to detecting that a clinical protocol is to be implemented. In this way, it can be confirmed with the user that the detection is reliable.

At block 204 of FIG. 2, it is identified which of a plurality of devices (e.g. medical devices) are required to implement the clinical protocol and one or more actions to perform in connection with the identified ones of the plurality of devices to implement the clinical protocol are also identified. More specifically, the one or more processors 102 of the apparatus 100 identify which of a plurality of devices are required to implement the clinical protocol and one or more actions to perform in connection with the identified ones of the plurality of devices to implement the clinical protocol. Thus, the one or more processors 102 of the apparatus 100 are able to detect what clinical protocol is to be implemented and which devices and actions need to be taken to implement that clinical protocol. In this way, the complexity of implementing the clinical protocol is reduced.

In some embodiments, the one or more processors 102 of the apparatus 100 may be configured to identify which of the plurality of devices are required to implement the clinical protocol by being configured to compare the clinical protocol to a plurality of (e.g. a collection of) clinical protocols stored in one or more memories 106 with an indication of at least one device that is required to implement the clinical protocol and one or more actions that the at least one device is required to perform to implement the clinical protocol (e.g. in the form of a look-up table). A memory 106 that is configured to store a plurality of clinical protocols may be referred to as a protocol database. In some embodiments, the apparatus 100 may comprise at least one of these memories 106. Alternatively or in addition, at least one of these memories 106 may be external to (e.g. separate to or remote from) the apparatus 100.

In some embodiments, the one or more actions to perform in connection with the identified ones of the plurality of devices to implement the clinical protocol may, for example, comprise one or more actions that the identified ones of the plurality of devices are required to perform to implement the clinical protocol and/or one or more actions that the user is required to perform in connection with the identified ones of the plurality of devices to implement the clinical protocol.

At block 206 of FIG. 2, a user interface 104 is controlled to output one or more notifications on the manner in which a user is to interact with one or more of the identified ones of the plurality of devices and/or one or more of the identified ones of the plurality of devices are controlled to cause the one or more identified actions to be performed in connection with the identified ones of the plurality of devices to implement the clinical protocol. More specifically, the one or more processors 102 of the apparatus 100 control a user interface 104 to output the one or more notifications and/or control one or more of the identified ones of the plurality of devices to cause the one or more identified actions to be performed in this way.

In an example, the one or more notifications on the manner in which a user is to interact with one or more of the identified ones of the plurality of devices may comprise an instruction for the user to trigger (e.g. by a press of a button on the user interface 104) the one or more identified actions to be performed in connection with the identified ones of the plurality of devices to implement the clinical protocol. In this example, in response to the user triggering the one or more identified actions (e.g. by pressing the button on the user interface 104), the one or more identified actions may be re-routed to the one or more of the identified ones of the plurality of devices to cause the identified ones of the plurality of devices to perform the one or more identified actions to implement the clinical protocol. Thus, in this example, a command by the user triggers an actual event on the device(s) and/or system(s).

The one or more notifications that the user interface 104 is controlled to output can be simplified compared to options (e.g. of a menu or screen structure) output by a user interface of any of the plurality of devices. For example, in some embodiments, a number of notifications that the user interface 104 is controlled to output may be less than a number of options that a user needs to navigate through on a user interface of one or more of the plurality of devices in order to implement the same clinical protocol. In this way, time is saved since the user does not need to navigate through a large number of options on complex menus and screen structures output by any of the plurality of devices themselves in order to complete the task at hand. By way of the one or more notifications that the user interface 104 is controlled to output, the user can be provided with simplified controls that are only relevant to the clinical protocol that is to be implemented. This also allows for a consistent user experience (e.g. in terms of look and feel of the user interface) across different types of devices from different vendors. For example, the one or more notifications (e.g. one or more buttons) may be the same color (e.g. blue) in every step of the clinical protocol. In this way, the usability can be improved.

In some embodiments, the one or more processors 102 of the apparatus 100 may be configured to control one or more of the identified ones of the plurality of devices by being configured to transmit (e.g. via the communications interface 110) a signal to one or more of the identified ones of the plurality of devices to trigger the one or more of the identified ones of the plurality of devices to perform one or more of the identified actions. The one or more of the identified ones of the plurality of devices can be configured to (e.g. automatically) perform the one or more of the identified actions in response to receiving the signal. The signal may, for example, be sent over a network. In some embodiments, the signal may comprise (or include) an application programming interface (API) or a technical protocol for use by the one or more of the identified ones of the plurality of devices in performing the one or more of the identified actions.

As mentioned earlier, in some embodiments, the apparatus 100 may comprise the user interface 104 that is controlled at block 206 of FIG. 2 to output the one or more notifications. Alternatively, the user interface 104 that is controlled at block 206 of FIG. 2 to output the one or more notifications may be external to (e.g. separate to or remote from) the apparatus 100. In some embodiments, the user interface 104 that is controlled at block 206 of FIG. 2 to output the one or more notifications can be a user interface of one of the plurality of devices. In other embodiments, the user interface 104 that is controlled at block 206 of FIG. 2 to output the one or more notifications may be separate to the plurality of devices.

The user interface 104 that is controlled at block 206 of FIG. 2 to output the one or more notifications can comprise an actual (i.e. physical) user interface according to some embodiments, e.g. the user interface may be a GUI. In these embodiments, the user interface can be a different user interface to a user interface of the plurality of devices or a user interface of one or more of the plurality of devices. In some embodiments where the user interface is the user interface of one or more of the plurality of devices, the one or more processors 102 of the apparatus 100 can be configured to control the user interface of one or more of the plurality of devices to output the one or more notifications on the manner in which the user is to interact with one or more of the identified ones of the plurality of devices. For example, the one or more notifications may replace information previously provided on the user interface of one or more of the plurality of devices (e.g. to add new features that may be relevant to the clinical protocol or to remove features that are no longer relevant). The user interface of one or more of the plurality of devices may be reskinned in this way, e.g. to modernize it, such as based on latest design language. The visual look and feel of the user interface of one or more of the plurality of devices can be updated or the entire user interface of one or more of the plurality of devices can be replaced in this way. In this way, the usability is improved.

In other embodiments, the user interface 104 that is controlled at block 206 of FIG. 2 to output the one or more notifications can comprise a virtual user interface, e.g. the user interface 104 may be a pair of AR glasses configured to be worn by the user. In some embodiments where the user interface 104 that is controlled at block 206 of FIG. 2 to output the one or more notifications comprises a virtual user interface, the one or more processors 102 of the apparatus 100 may be configured to render the virtual user interface over (e.g. on top of) at least part of a user interface of one or more of the plurality of devices. For example, the one or more notifications may at least partially cover the information provided on the user interface of one or more of the plurality of devices (e.g. to add new features that may be relevant to the clinical protocol or to hide features that are no longer relevant). The user interface of one or more of the plurality of devices may be reskinned in this way, e.g. to modernize it, such as based on latest design language. The visual look and feel of the user interface of one or more of the plurality of devices can be updated or the entire user interface of one or more of the plurality of devices can be replaced in this way.

In an example, the virtual interface may be controlled to render a notification as an instruction overlaying a button (e.g. an on/off button) of a user interface of one or more of the plurality of devices that instructs the user to press the button (e.g. to turn on or off one or more of the plurality of devices). The notification may disappear once the action of pressing the button is completed by the user. The next action may then be shown. Thus, the virtual user interface may at least partially overlay (or at least partially mask) a user interface of one or more of the plurality of devices according to some embodiments. In effect, at least part of a user interface of one or more of the plurality of devices can be reskinned. In this way, the user interface of one or more of the plurality of devices over which the virtual user interface is rendered can be optimized for the clinical protocol to be implemented. Moreover, this is possible without changing any of the actual devices.

In some embodiments, the one or more processors 102 of the apparatus 100 may be configured to control the user interface 104 to output the one or more notifications next to the identified ones of the plurality of devices with which the user is to interact. For example, in some embodiments where the user interface 104 that is controlled at block 206 of FIG. 2 to output the one or more notifications comprises a virtual user interface, the one or more processors 102 of the apparatus 100 may be configured to render the virtual user interface next to the identified ones of the plurality of devices with which the user is to interact, such that the one or more notifications are output next to the identified ones of the plurality of devices with which the user is to interact.

In some embodiments where the user interface 104 that is controlled at block 206 of FIG. 2 to output the one or more notifications comprises an actual (i.e. physical) user interface, the actual user interface may be positioned next to the identified ones of the plurality of devices with which the user is to interact, such that when the one or more processors 102 of the apparatus 100 are configured to control the user interface 104 to output the one or more notifications, the one or more notifications are output next to the identified ones of the plurality of devices with which the user is to interact. The one or more notifications that are output next to the identified ones of the plurality of devices can, for example, comprise instructions (e.g. labelled text instructions).

In some embodiments where the one or more processors 102 of the apparatus 100 are configured to control the user interface 104 to output the one or more notifications, the one or more processors 102 of the apparatus 100 can be configured to control the user interface 104 to output the one or more notifications in an order that is defined by the clinical protocol and/or in a plurality of different steps. Alternatively or in addition, in some embodiments where the one or more processors 102 of the apparatus 100 are configured to control one or more of the identified ones of the plurality of devices, the one or more processors 102 of the apparatus 100 can be configured to control the one or more of the identified ones of the plurality of devices in an order that is defined by the clinical protocol and/or in a plurality of different steps.

Although not illustrated in FIG. 2, in some embodiments, the one or more processors 102 of the apparatus 100 may be configured to check at least one memory 106 that is configured to store an indication of which of a plurality of devices is available (e.g. currently connected) to identify which of the identified ones of the plurality of devices are available. Thus, in some embodiments, at least one memory 106 may be configured to store an indication of which of a plurality of devices is available (e.g. currently connected). In some embodiments, the at least one memory 106 may also be configured to store an indication of which of a plurality of devices is unavailable (e.g. currently disconnected). In some embodiments, the one or more processors 102 of the apparatus 100 may be configured to, only for the identified ones of the plurality of devices that are available, control the user interface 104 to output the one or more notifications and/or control one or more of the identified ones of the plurality of devices.

In some embodiments, for each of the plurality of devices, an indication of whether the device is available may be stored with information identifying the device, such as a device name, a vendor name, a device type, an internet protocol (IP) address, or any other information, or any combination of information, which can identify the device. A memory 106 that is configured to store an indication of which of the plurality of devices are available may be referred to as a device database. In some embodiments, the apparatus 100 may comprise at least one of these memories 106. Alternatively or in addition, at least one of these memories 106 may be external to (e.g. separate to or remote from) the apparatus 100.

Although also not illustrated in FIG. 2, in some embodiments, the one or more processors 102 of the apparatus 100 may be configured to acquire, from the at least one sensor 108 (as described earlier), a signal indicative of one or more actions of the user. For example, in some embodiments, the one or more processors 102 of the apparatus 100 may be configured to track one or more actions of the user. As mentioned earlier, the apparatus 100 may comprise at least one sensor 108 and/or the at least one sensor 108 may be external to (e.g. separate to or remote from) the apparatus 100.

In some embodiments where a signal indicative of one or more actions of the user is acquired, the one or more processors 102 of the apparatus 100 may also be configured to control the user interface 104 to render guidance (e.g. step-by-step guidance) based on the one or more actions of the user to guide the user in their interaction with one or more of the identified ones of the plurality of devices. For example, the one or more processors 102 of the apparatus 100 may be configured to render guidance by being configured to control the user interface 104 to change the one or more output notifications based on the one or more actions of the user (e.g. as the user performs different steps of the clinical protocol). In this way, the apparatus 100 can help to guide the user (e.g. on a step-by-step basis) across the one or more actions and devices with a single user interface 104. Thus, even inexperienced or untrained users can operate the devices.

There is also provided a system comprising the apparatus 100 described herein and the plurality of devices. The apparatus 100 can be configured to communicate with the plurality of devices (e.g. via the communications interface 106). Similarly, the plurality of device can be configured to communicate with the apparatus 100.

In some embodiments, one or more of the plurality of devices can be configured to notify the apparatus 100 of their status (e.g. a part needs replacing or has been replaced). Thus, in some embodiments, the one or more processors 102 of the apparatus 100 can be configured to receive an indication of the status of one or more of the plurality of devices. In some of these embodiments, the one or more processors 102 of the apparatus 100 may be configured to control the user interface 104 to output one or more notifications on the manner in which a user is to interact with one or more of the identified ones of the plurality of devices and/or control one or more of the identified ones of the plurality of devices to cause the one or more identified actions to be performed in connection with the identified ones of the plurality of devices to implement the clinical protocol based on the status of one or more of the plurality of devices.

Figure 3:
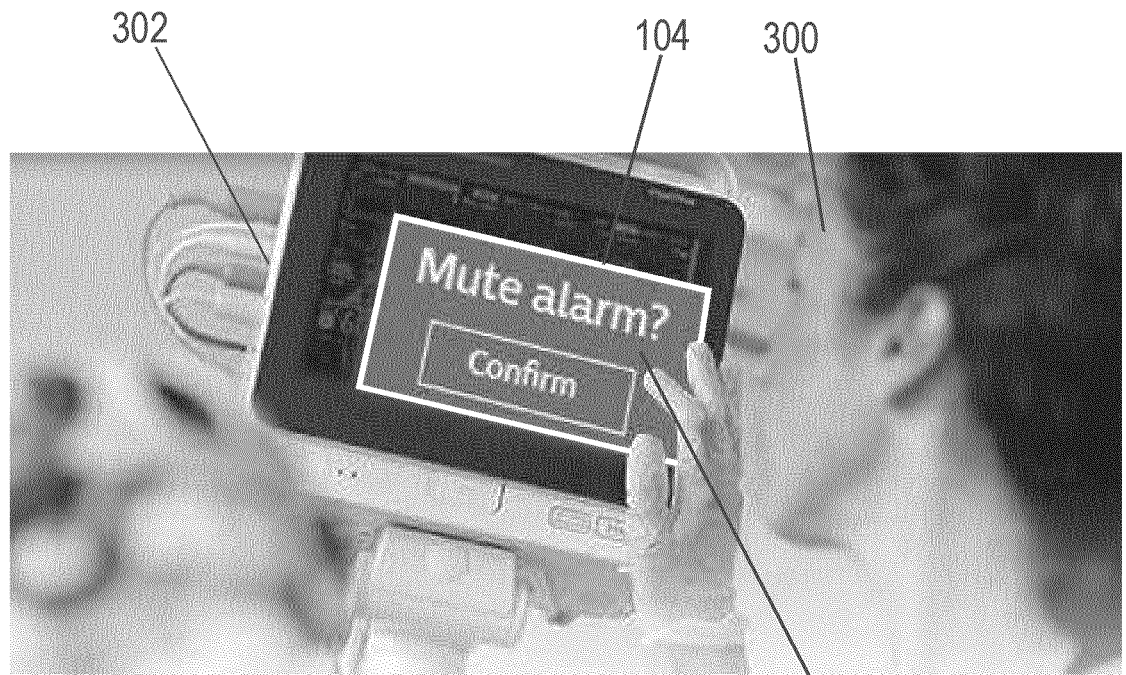
FIGS. 3 and 4 are illustrations of a user interface according to an example.
Figure 4:
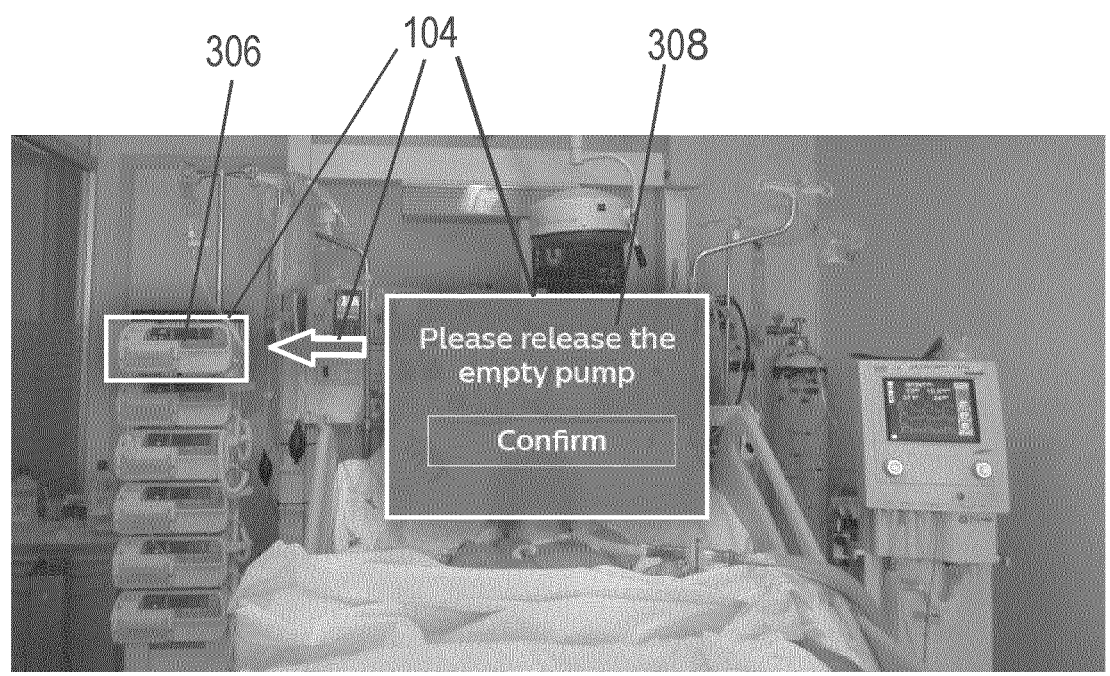

FIGS. 3 and 4 illustrate a user interface 104 according to an example. In the illustrated example, a user 300 is required to implement a clinical protocol. The user may be a nurse, such as a nurse of an intensive care unit (ICU). The user may be responsible for taking care of multiple subjects. The user may have limited experience of operating a plurality of devices to be used in implementing the clinical protocol. For example, the user may be straight out of medical school.

As described earlier, one or more processors 102 of the apparatus 100 described herein (not illustrated in FIG. 3 or 4) detect that a clinical protocol is to be implemented and identify which of a plurality of devices are required to implement the clinical protocol and one or more actions to perform in connection with the identified ones of the plurality of devices to implement the clinical protocol. Initially, in this illustrated example, the one or more processors 102 of the apparatus 100 control the user interface to output a notification on the manner in which the user is to interact with one or more of the identified ones of the plurality of devices.

In more detail, in this illustrated example, an alarm of a bedside monitor 302 of a subject goes off. The bedside monitor 302 shows that an identified one of the plurality of devices (namely, a pump) 306 is empty and needs to be replaced, and recalibrated. The user 300 puts on a pair of AR glasses (not illustrated) and a virtual user interface 104 appears in front of the user 300. The virtual user interface 104 is output over an original user interface of the bedside monitor 302. As illustrated in FIG. 3, the one or more processors 102 of the apparatus 100 control the virtual user interface 104 to output a notification 304 on the manner in which the user 300 is to interact with one or more of the identified ones of the plurality of devices 302. In this illustrated example, the notification 304 indicates that the user needs to first mute the alarm of the bedside monitor 302. The virtual user interface 104 only outputs a single "Confirm" button that the user 300 can press to mute the alarm, whereas the user 300 previously needed to click on many different options on a complex menu screen on the original user interface of the bedside monitor 302. Thus, the process of muting the alarm is simplified and made more efficient for the user.

Then, the one or more processors 102 of the apparatus 100 described herein control one or more of the identified ones of the plurality of devices 302 to cause the one or more identified actions to be performed in connection with the identified ones of the plurality of devices 302 to implement the clinical protocol. In more detail, when the user 300 presses the "Confirm" button on the virtual user interface 104 as illustrated in FIG. 3, the one or more processors 102 of the apparatus 100 detect this and then control the bedside monitor 302 to mute the alarm, e.g. by accessing the bedside monitor 302 via its API to trigger a 'mute alarm' function.

In this illustrated example, the one or more processors 102 of the apparatus 100 are configured to control the user interface 104 to output the one or more notifications in an order that is defined by the clinical protocol. Thus, next, the one or more processors 102 of the apparatus 100 again control the virtual user interface 104 to output a notification 308 on the manner in which the user 300 is to interact with one or more of the identified ones of the plurality of devices 306. In this illustrated example, the notification 308 is an arrow that points towards the pump 306 and indicates that the empty pump needs to be released. Although the user 300 is unable to reach the button on the actual pump 306 to release it, the virtual user interface 104 is in reaching distance of the user 300 and the notification 308 output on the virtual user interface 104 comprises a single "Confirm" button that the user 300 can press to release the pump 306. Thus, the user can easily press the "Confirm" button to release the pump 306.

Although not illustrated in FIGS. 3 and 4, after pressing the "Confirm" button, the one or more processors 102 of the apparatus 100 may be configured to control the virtual user interface 104 to output a notification on the manner in which a user 300 is to interact with the pump 306, such as a notification to explain that the user 300 needs to remove the empty pump 306 and replace it will a full one. When a new pump has been added, the system logs this signal and the one or more processors 102 of the apparatus 100 described herein are notified by the system. The one or more processors 102 of the apparatus 100 may be configured to then control the virtual user interface 104 to output a notification on the manner in which a user 300 is to indicate that the user 300 needs to calibrate the pump 306. Normally, it takes many clicks to start the calibration, but since the one or more processors 102 of the apparatus 100 are aware of the clinical protocol, the virtual user interface 104 can be updated with a slider and a button. The user 300 then only needs to use the slider to set the threshold of the offset and the button to confirm this setting.

Then, the one or more processors 102 of the apparatus 100 described herein may again control one or more of the identified ones of the plurality of devices to cause the one or more identified actions to be performed in connection with the identified ones of the plurality of devices to implement the clinical protocol. In more detail, after setting the threshold and pressing the button, the one or more processors 102 of the apparatus 100 may control the new pump to start the calibration process. This is the end of the clinical protocol and thus the virtual interface 104 may disappear. In addition, data acquired during the clinical protocol may be logged, e.g. in an electronic medical record (EMR).

There is also provided a computer program product comprising a computer readable medium. The computer readable medium has computer readable code embodied therein. The computer readable code is configured such that, on execution by a suitable computer or processor, the computer or processor is caused to perform the method described herein. The computer readable medium may be, for example, any entity or device capable of carrying the computer program product. For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

There is thus provided herein an improved apparatus 100, method 200, and computer program product for implementing a clinical protocol, which addresses the limitations associated with the existing techniques. The improved apparatus 100, method 200, and computer program product described herein allows the user to control multiple devices in an optimized user interface that is aware of the protocol at hand. This saves time and also reduces complexity compared to the existing user interfaces. The apparatus 100 described herein can thus be used by untrained or inexperienced users. Multiple devices can be used at the same time to implement a clinical protocol without the need for the users to be experienced or have knowledge of the manner in which the devices need to be operated to implement the clinical protocol. Moreover, the improvements are achieved without the need to update or change any devices and, in some cases, even without the need for the user to touch any devices. This avoids any destabilization the devices (or the independent function of those devices) and also avoids the need for additional processes such as FDA approval.

The apparatus 100, system, method 200, and computer program product described herein can be useful in a variety of settings in which a clinical protocol is to be implemented using multiple devices and particular, for example, in environments where multiple devices have different user interfaces and/or need to be operated in a particular manner (such as in a certain order). For example, the apparatus 100, method 200, and computer program product described herein can be useful in a hospital setting (e.g. in an intensive care unit, ICU) or any other setting in which a clinical protocol is to be implemented using multiple devices.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for implementing a clinical protocol, the apparatus comprising:
a plurality of different clinical devices operable by a medical practitioner;
at least one camera configured to monitor gestures of the user during operation of the plurality of different clinical devices; and
one or more processors configured to:
detect that a clinical protocol is to be implemented;
identify, based on the gestures of the user monitored by the at least once camera, which of a plurality of devices are required to implement the clinical protocol and one or more actions to perform in connection with the identified ones of the plurality of different devices to implement the clinical protocol;
control a user interface to output one or more notifications related to the manner in which a user is to interact with one or more of the identified ones of the plurality of different devices and control one or more of the identified ones of the plurality of different devices to cause the one or more identified actions to be performed in connection with the identified ones of the plurality of different devices to implement the clinical protocol; and
automatically transmit, independently of user interactions with the user interface, a signal to the one or more of the identified ones of the plurality of different devices to perform at least one of the identified actions.

2. The apparatus as claimed in claim 1, wherein:
the user interface is separate to the plurality of different devices.

3. The apparatus as claimed in claim 1, wherein:
the one or more processors are configured to:
identify which of a plurality of different devices are required to implement the clinical protocol by being configured to:
compare the clinical protocol to a plurality of clinical protocols stored in one or more memories with an indication of at least one device among the plurality of different devices that is required to implement the clinical protocol and one or more actions that the at least one device is required to perform to implement the clinical protocol.

4. The apparatus as claimed in claim 1, wherein:
the one or more processors are configured to:
control the user interface to output the one or more notifications in an order that is defined by the clinical protocol; and/or
control one or more of the identified ones of the plurality of different devices in an order that is defined by the clinical protocol.

5. The apparatus as claimed in claim 1, wherein:
the one or more processors are configured to:
control the user interface to output the one or more notifications in a plurality of different steps; and/or
control one or more of the identified ones of the plurality of different devices in a plurality of different steps.

6. The apparatus as claimed in claim 1, wherein:
the one or more processors are configured to:
check at least one memory that is configured to store an indication of which of a plurality of different devices is available to identify which of the identified ones of the plurality of different devices are available; and
only for the identified ones of the plurality of different devices that are available, control the user interface to output the one or more notifications and/or control one or more of the identified ones of the plurality of different devices.

7. The apparatus as claimed in claim 1, wherein:
the one or more processors are configured to:
control the user interface to output the one or more notifications next to the identified ones of the plurality of different devices with which the user is to interact.

8. The apparatus as claimed in claim 1, wherein:
the user interface comprises a virtual user interface; and
the one or more processors are configured to:
render the virtual user interface over at least part of a user interface of one or more of the plurality of different devices.

9. The apparatus as claimed in claim 1, wherein:
the signal comprises an application programming interface or a technical protocol for use by the one or more of the identified ones of the plurality of different devices in performing the one or more of the identified actions.

10. The apparatus as claimed in claim 1, wherein:
the one or more processors are configured to:
acquire, from at least one sensor, a signal indicative of one or more actions of the user; and
control the user interface to render guidance based on the one or more actions of the user to guide the user in their interaction with one or more of the identified ones of the plurality of different devices.

11. The apparatus as claimed in claim 1, wherein:
the one or more actions to perform in connection with the identified ones of the plurality of different devices to implement the clinical protocol comprise:
one or more actions that the identified ones of the plurality of different devices are required to perform to implement the clinical protocol; and/or
one or more actions that the user is required to perform in connection with the identified ones of the plurality of different devices to implement the clinical protocol.

12. The apparatus of claim 1, wherein:
the one or more processors are configured to:
control the user interface to render a request as to whether the clinical protocol is to be implemented.

13. A computer-implemented method for implementing a clinical protocol, the method comprising:
using at least one camera to monitor the gestures of a medical practitioner operating a plurality of different devices in a clinical setting;
detecting, by at least one processor, that a clinical protocol is to be implemented;
identifying, by the at least one processor, from the gestures of the medical practitioner monitored by the at least one sensor, which of the plurality of different devices are required to implement the clinical protocol and one or more actions to perform in connection with the identified ones of the plurality of different devices to implement the clinical protocol;
controlling, by the at least one processor, a user interface to output one or more notifications on the manner in which a user is to interact with one or more of the identified ones of the plurality of different devices and/or controlling one or more of the identified ones of the plurality of different devices to cause the one or more identified actions to be performed in connection with the identified ones of the plurality of different devices to implement the clinical protocol; and automatically transmitting, by the at least one processor and independently of user interactions with the user interface, a signal to the one or more of the identified ones of the plurality of different devices to perform at least one of the identified actions.

14. An apparatus for implementing a clinical protocol, the apparatus comprising:
a plurality of different clinical devices operable by a medical practitioner;
at least one camera configured to monitor gestures of the user during operation of the plurality of different clinical devices
one or more processors configured to:
detect that a clinical protocol is to be implemented;
identify, based on the gestures of the user monitored by the at least once camera, which of a plurality of devices are required to implement the clinical protocol and one or more actions to perform in connection with the identified ones of the plurality of devices to implement the clinical protocol; and
control a user interface to output one or more notifications related to the manner in which a user is to interact with one or more of the identified ones of the plurality of devices and/or control one or more of the identified ones of the plurality of devices to cause the one or more identified actions to be performed in connection with the identified ones of the plurality of devices to implement the clinical protocol,
wherein the one or more processors are further configured to:
identify which of a plurality of devices are required to implement the clinical protocol by being configured to:
compare the clinical protocol to a plurality of clinical protocols stored in one or more memories with an indication of at least one device that is required to implement the clinical protocol and one or more actions that the at least one device is required to perform to implement the clinical protocol.

* * * * *